US012364264B2

(12) United States Patent
Moores

(10) Patent No.: US 12,364,264 B2
(45) Date of Patent: *Jul. 22, 2025

(54) INHIBITORS OF ENZYMES THAT CONFER PESTICIDE RESISTANCE

(71) Applicant: APRESLABS LTD., Harpenden (GB)

(72) Inventor: Graham Moores, Stevenage (GB)

(73) Assignee: APRESLABS LTD., Harpenden (GB)

( * ) Notice: Subject to any disclaimer, the term of this patent is extended or adjusted under 35 U.S.C. 154(b) by 513 days.

This patent is subject to a terminal disclaimer.

(21) Appl. No.: 17/405,796

(22) Filed: Aug. 18, 2021

(65) Prior Publication Data

US 2021/0368790 A1 Dec. 2, 2021

Related U.S. Application Data

(63) Continuation of application No. 15/743,069, filed as application No. PCT/EP2016/065794 on Jul. 5, 2016, now Pat. No. 11,122,801.

(30) Foreign Application Priority Data

Jul. 9, 2015 (GB) ..................................... 1512041

(51) Int. Cl.
| | |
|---|---|
| *A01N 37/06* | (2006.01) |
| *A01N 25/22* | (2006.01) |
| *A01N 43/40* | (2006.01) |
| *A01N 43/50* | (2006.01) |
| *A01N 43/78* | (2006.01) |
| *A01N 53/00* | (2006.01) |
| *C12N 9/99* | (2006.01) |

(52) U.S. Cl.
CPC ............. *A01N 37/06* (2013.01); *A01N 25/22* (2013.01); *A01N 43/40* (2013.01); *A01N 43/50* (2013.01); *A01N 43/78* (2013.01); *A01N 53/00* (2013.01); *C12N 9/99* (2013.01); *A01N 2300/00* (2013.01)

(58) Field of Classification Search
CPC ........ A01N 25/22; A01N 37/06; A01N 43/40; A01N 53/00; A01N 2300/00; C12N 9/99
See application file for complete search history.

(56) References Cited

U.S. PATENT DOCUMENTS

| | | | |
|---|---|---|---|
| 4,826,678 A | 5/1989 | Gaudet et al. | |
| 4,861,762 A | 8/1989 | Puritch et al. | |
| 4,983,591 A | 1/1991 | Puritch et al. | |
| 5,422,371 A | 6/1995 | Liao et al. | |
| 5,700,473 A | 12/1997 | Puritch | |
| 5,942,542 A | 8/1999 | Killick et al. | |
| 8,658,223 B2 | 2/2014 | Willis et al. | |
| 11,122,801 B2 * | 9/2021 | Moores | A01N 53/00 |
| 2004/0157803 A1 | 8/2004 | Williams et al. | |
| 2005/0244445 A1 | 11/2005 | Anderson | |
| 2010/0069314 A1 | 3/2010 | Qin et al. | |
| 2013/0101687 A1 | 4/2013 | Willis | |
| 2014/0005423 A1 | 1/2014 | Allen | |

FOREIGN PATENT DOCUMENTS

| | | |
|---|---|---|
| CN | 1649578 A | 8/2005 |
| CN | 101449675 B | 9/2011 |
| CN | 102215694 A | 10/2011 |
| CN | 102524246 A | 7/2012 |
| CN | 102934645 A | 2/2013 |
| CN | 103651380 A | 3/2014 |
| CN | 104757015 A | 7/2015 |
| CN | 014823972 A | 8/2015 |
| CN | 104823972 A | 8/2015 |
| EP | 2341097 A1 | 7/2011 |
| FR | 2634103 A1 | 1/1990 |
| GB | 2070430 A | 9/1981 |
| GB | 2160216 A | 12/1985 |
| JP | 2011-251922 A | 12/2011 |
| WO | 90/03730 A1 | 4/1990 |
| WO | 91/10371 A1 | 7/1991 |
| WO | 94/01100 A1 | 1/1994 |
| WO | 97/12515 A1 | 4/1997 |
| WO | 03/075656 A2 | 9/2003 |
| WO | 2013/010099 A1 | 1/2013 |
| WO | 2014/066466 A1 | 5/2014 |

OTHER PUBLICATIONS

UK Search Report for Application No. GB1512041.3, issued Dec. 21, 2015.
International Search Report and Written Opinion from the European Patent Office for Application No. PCT/EP2016/065794, issued Aug. 16, 2016.
Kepler et al., *Biohydrogenation of Unsaturated Fatty Acids*, The Journal of Biological Chemistry, vol. 245, No. 14, 1970, pp. 3612-3620.
Yao et al., *The Inhibitory Effect of Polyunsaturated Fatty Acids on Human CYP Enzymes*, Nov. 25, 2006, Life Sciences, pp. 2432-2440.
James et al., *The inhibition of Unsaturated Fatty Acid Biosynthesis in Plants by Sterculic Acid*, European Journal of Biochemistry, vol. 3, 1968, pp. 318-325.
Chinese Office Action dated Mar. 10, 2020 for Application No. 201680050038.
Chinese Search Report dated Mar. 2, 2020 for Application No. 201680050038.
Great Britain Office Action dated Jan. 14, 2021 for Application No. GB1611701.2.
Great Britain Office Action dated May 19, 2020 for Application No. GB1611701.
Chung et al., Nutrition Research and Practise, vol. 7 (4), 2013 "Effects of Perilla Oil on Plasma Concentrations of Cardioprotective (n-3) Fatty Acids and Lipid Profiles in Mice", pp. 256-261.
Mulrooney, J. E.; et al., "Rainfastening of Bifenthrin to Cotton Leaves with Selected Adjuvants," J. Environ. Qual. 29:1863-66 (2000).
GB Examination Report, dated Oct. 6, 2020, for Application No. GB1611701.2.

(Continued)

*Primary Examiner* — Theodore R. Howell
(74) *Attorney, Agent, or Firm* — The Dobrusin Law Firm, P.C.

(57) ABSTRACT

The use of a C6 to C24 mono- and polyunsaturated acids or their derivatives thereof enzyme inhibitors particularly as P450 and esterase inhibitors in pesticide formulations.

8 Claims, 5 Drawing Sheets

(56) References Cited

OTHER PUBLICATIONS

Schilder, A., "Effect of water pH on the stability of pesticides," Michigan State University Extension, Department of Plant Pathology, Mar. 18, 2008.
EPO Summons to attend oral proceedings pursuant to Rule 115(1) EPC, dated Jan. 24, 2024, for European Application 16735860.5.
Communication pursuant to article 94(3) EPC, dated Nov. 10, 2020, for European Application 16735860.5.

* cited by examiner

INHIBITORS OF ENZYMES THAT CONFER PESTICIDE RESISTANCE

FIELD OF THE INVENTION

The present invention relates to synergists for pesticides, and more particularly, to the use of inhibitors to increase the effectiveness of pesticides.

SUMMARY

The present invention relates to synergists for pesticides, and the term pesticides as used herein includes insecticides, fungicides and herbicides. The effectiveness of pesticides can be reduced by enzymes that metabolise the pesticides and confer pesticide resistance. Accordingly the term synergist as used herein refers to inhibitors of those enzymes that metabolise pesticides and thus confer pesticide resistance. The invention is particularly useful with insecticides. In particular the invention relates to the use of inhibitors for the enzymes of the P450 and esterase classes to increase the effectiveness of pesticides and in particular insecticides based on pyrethroids and neonicotinoids. The Synergists also increase the effectiveness of fungicides and herbicides. In particular the invention is concerned with the use of naturally occurring materials or materials derived therefrom as synergists for the pesticides. The present invention is particularly useful with agricultural pesticides, disease vectors and animal health and especially synthetic pyrethroids.

DETAILED DESCRIPTION

Figure 1:
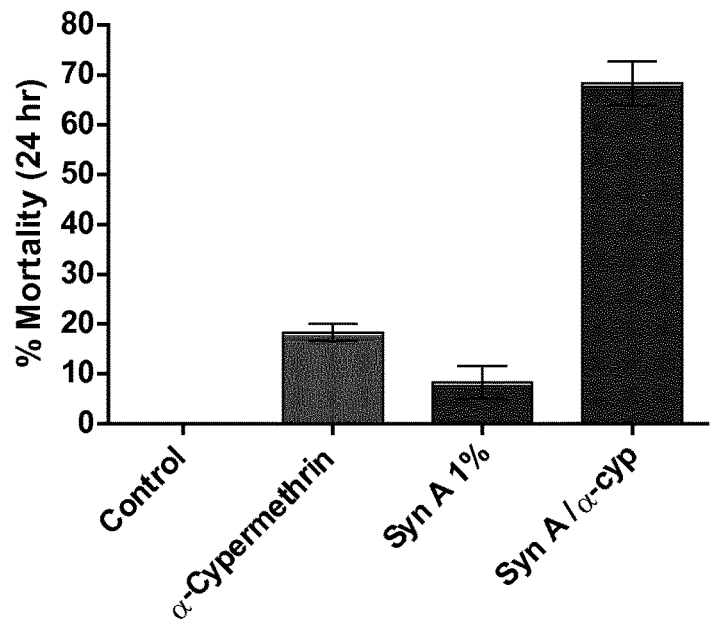
FIG. 1 is a graph illustrating the mortality rates of Example 1.

The synergists of this invention are useful with a range of pesticides and we have found that their use results in improved efficacy is exhibited for a range of pesticides.

Examples of pesticides to which this invention may be applied include:

Organophosphates such as profenofos, sulprofos, methyl parathion, azinphos-methyl, demeton-s-methyl, Dichlorvos, omethoate, heptenophs, thiometon, fenamiphos, monocrotophos, profenophos, triazophos, methamidophos, dimethoate, phosphamidon, malathion, chloropyrifos, mevinphos, ethion, trichlorfon, disulfoton, oxydemeton-methyl, fenthion, phenthoate, vamidothion, phosalone, terbufos, fensulfothion, fonofos, phorate, phoxim, pirimiphos-methyl, dicrotofos, phosmet, ethoprophos, fenamiphos, methadithion, acephate, isozathion, chlormephos, thiometon, cadusafos, pyraclofos, terbupirimfos, chlorethoxyfos, pirimiphos-ethyl, fenitrothion or diazinon.

The invention is however particularly useful with neonicotinoids and pyrethroids both natural and synthetic. Synthetic pyrethroids are pyrethroids which are not found in naturally occurring material. The invention is particularly useful with synthetic pyrethroids such as permethrin, esfenvalerate, fevalerate, deltamethrin, cyhalothrin in particular lambda-cyhalothrin, bifenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3furylmethyl-(E)-1R,35)-2,2-dimethyl-3-(2-oxothiolan-3-ylidenemethyl) cyclopropane carboxylate, cypermethrins, flucythrinate, fluvalinate, tralomethrin, allethrin, tetramethrin, bioallethrin, cycloprothrin, tefluthrin, acrinathrin or zeta cypermethrin.

Carbamates (including aryl carbamates) such as pirimicarb, cloethocarb, carbofuran, furathiocarb, ethiofencarb, aldicarb, thiofurox, carbosulfan, bendiocarb, fenobucarb, propoxur, carbaryl, methomyl, cartap, formetanate, xylylcarb, xylyl methylcarbamate, Isoprocarb, thiodicarb, fenoxycarb, benfuracarb, alanycarb or oxamyl;

Biopesticides such as *Bacillus thuringiensis*.

Neonicotinoids, such as Imidacloprid, Acetamiprid, Nitenpyram, Thiametoxam, or Thiacloprid.

The synergists may also be used with fungicides such as, but not limited to, benomyl, carbendazim, cyprodinil, chlorthalonil, dimethomorph, edifenphos, fenpropimorph, metalaxyl, (R)-metalaxyl (enantiomer), oxadixyl, pyrifenox, thiabendazol, tridemorph, azoxystrobin, kresoxim-methyl or triazoles such as propiconazol, difenoconazol, bromoconazol, cyproconazole, epoxyconazol, hexaconazol, ipconazol, fenbuconazol, myclobutanil, penconazol, tebuconazol, triadimefon, triadimenol, tetraconazol, triticonazol, or uniconazol; furtheron acibenzolar-S-methyl, famoxadone, quinoxyfen, spiroxamin, fludioxonil, fenpiclonil, fenhexamid and 2-[.alpha.-{[(alpha.-methyl-3-trifluoromethyl-benzyhimino]-oxy}-o-tolyl]-glyoxylic acid-methylester-O-methyloxim. Preference is given to carbendazim, cyprodinil, chlorthalonil, metala,yl, (R)-metalaxyl, oxadixyl, azoxystrobin, kresoxim-methyl, propiconazol, cyproconazole, epoxyconazol and tebuconazol, including all: Strobilurins, Dithiocarbamates, Phthalimides/nitriles, Triazoles, Inorganics, Phenylamides, Anilinopyrimidines, Dicarboxamides, Organophosphates, Benzimidazoles, Morpholines, Carboxamides and other fungicides.

Additionally the synergists may be used with herbicides such as chlortoluron, bifenox, bromoxynil and its octanoate, ioxynil and its octanoate, fluometuron, glufosinate, glyphosate, pendimetalin, sulcotrione, 3-phenyl-4-hydroxy-6-chlorpyridazine, alachlor, dimethenamide, metolachlor, (S)-metolachlor (enantiomer), or sulfonyl-ureas such as bensulfuron, primisulfuron, prosulfuron, triasulfuron, pyrazosulfuron, nicosulfuron, rimsulfuron, thifensulfuron, triflusulfuron, oxasulfuron, cinosulfuron; furtheron atrazine, propaquizafop, trinexapac-ethyl, pyridate, dicamba, clodinafop, fenclorin, fluometuron, glufosinate, glyphosate, sulcotrione, 3-phenyl-4-hydroxy-6-chlorpyridazin, dimethenamid, metolachlor, (S)-metolachlor, triasulfuron, nicosulfuron or rimsulfuron, including all: Phenoxies, Ureas, Triazines, Thiocarbamates, Bipyridyls, Hydroxybenzonitriles, Thiocarbamates, Carbamates, Pyridines, Dinitroanilines, Pyridazines, Chloracetanilides, Acetamides, Amino acid derivatives, Diphenyl Ethers, Cyclohexanediones, Aryloxyphenoxypropionates, Sulfonylureas, Imidazolinones, Oxyacetamides, It is well known that insects, fungae and plants (such as grasses and weeds) produce P450 and esterase enzymes which provide resistance to pesticides (see Oppenoorth F5

1985 Biochemistry and Genetics in Insecticide Resistance in Comprehensive Inect Physiology, Biochemistry and Pharmacology), resulting in either resistance to the pesticide or the need to use larger amounts of the pesticide which is both costly and environmentally undesirable.

Research on insect P450 and esterase enzymes has been, until recently, heavily slanted towards insecticide metabolism and resistance. P450 and esterase enzymes are one of the major tools used by insects to metabolise insecticides, mostly as a mechanism of detoxification, but also as a mechanism of bioactivation. P450 and esterase enzymes can detoxify and bioactivate at the same time. Such is the case for phosphorothioate insecticides, where the balance between the two outcomes is a function of both the chemical and the P450 enzyme. P450 and esterase enzymes are also the target of a commercially significant synergist, piperonyl butoxide (PBO). The knowledge concerning P450 in relation to insecticides is therefore devoted to metabolism, synergism and resistance.

It is standard practice in some countries (not Europe) to use the P450 inhibitor PBO with insecticides such as pyrethroids and neonicotinoids, however, as set out in Pest Manag Sci (2014) in a paper by Rene Fegereisen entitled "Insect P450 inhibitors and insecticides: challenges and opportunities", piperonyl butoxide (PBO) has its drawbacks and there remains a need for an environmentally safe and effective P450 inhibitor for insecticides such as pyerthroids and neonicotonides.

In an Article in Pest Mang Sci 2012 68 178-184 several selected natural compounds were investigated to determine their potential to increase the potency of natural pyrethrum against houseflies *Musca domestica*. All the compounds tested were less effective as synergists for pyrethrum than PBO.

P450 enzymes play an important role in drug metabolism and drug interactions and therefore in the development of a new drug. Absorption, distribution, metabolism and excretion (ADME) programmes invariably test drug candidates against a battery of human P450 enzymes in order to optimise metabolic stability and minimise interactions with those P450s that are highly polymorphic. Beyond the role of P450 inhibition or induction in unintended, variable pharmacokinetics of a new drug, much research is also aimed at preventing drug interactions caused by dietary inducers and inhibitors, such as bergamotin in grapefruit juice, which inactivates the main P450 enzyme of human liver. In fungicides, CYP51 inhibitors (lanosterol 14-alpha demethylase inhibitors, or DMIs) are examples of a P450 enzyme which is targeted. P450 inhibitors have also been developed as significant plant growth regulators. For instance, gibberellin biosynthesis is inhibited by compounds such as paclobutrazol, resulting in stunted growth to the benefit of early fruit set. CYP707A is a key enzyme in the catabolism of abscissic acid and its inhibition may lead to new plant growth regulators.

For pesticides the contribution of enzymes to pesticide targets has been historically essential. However P450 or esterase inhibitors are not widely used in herbicides, even though herbicide targets are principally enzymes rather than receptors. The enzyme acetylcholinesterase was for a time the predominant target for insecticides (organophosphorous pesticides and carbamates), but its relative importance has been rapidly declining since the introduction of synthetic pyrethroids and then of neonicotinoids. Other enzymes and enzyme systems include chitin biosynthesis affected by inhibitors such as the benzoylphenylureas.

Accordingly current drugs/pesticides that are P450 inhibitors all target specific P450 enzymes that are involved in biosynthetic reaction. However, the most significant P450 inhibitor used in insect control is PBO an insecticide synergist targeting (non-specifically) xenobiotic metabolising P450 enzymes.

The mode of action of PBO on P450 is believed to involve firstly binding to the active site of the P450 and then metabolism to a pseudoirreversible inhibitor complex between a carbene radical of the methylenedioxyphenyl group and the ferrous iron of the P450. Because inhibition is dependent on metabolism, potency of inhibition will be dependent on the particular P450 enzyme, and PBO is not a 'universal' inhibitor that will inhibit all P450 enzymes equally. Inhibition by PBO leads to a loss of measurable P450, as the carbene-iron complex cannot be displaced by CO. In the classical Omura and Sato detection of P450 it is the reduced P450 CO complex at 450 nm that is measured.

Only a few insect P450 enzymes are currently known or suspected to participate in important physiological processes, and fewer still have been biochemically established to do so. Five P450 enzymes are known to participate in ecdysone biosynthesis, and these are products of the halloween genes in Drosophila.

In addition, CYP18A1 is a 26-hydroxylase/oxidase that contributes to ecdysone inactivation. This gene is duplicated in Lepidoptera. There are to date no concerted attempts to target enzymes of ecdysone synthesis specifically.

P450 genes involved in ecdysone biosynthesis which can be assayed in heterologous expression systems that can be used in a screening programme for inhibitors, preferably in conjunction with in vivo assays. Another class of insect P450 enzymes with a known physiological substrate are the CYP15 enzymes, the JH epoxidases that use methyl farnesoate (CYP15A1) or farnesoic acid (and its congeners; CYP15C1) as substrates. Inhibition of JH synthesis in larval stages can lead to precocious metamorphosis and in adult stages to a block of ovarian function. This broad target was validated by the discovery of precocenes, 45 compounds that in some insects can cause cytotoxicity and necrosis of the corpora allata, the glands that make JH. Targeting the last or penultimate step of JH synthesis with epoxidase inhibitors has been successful, at least in vitro. A number of papers have described the inhibition of JH synthesis by cockroach corpora allata with concomitant accumulation of methyl farnesoate. The inhibitors comprised most of the known functionalities necessary for P450 inhibition, methylenedioxyphenyl compounds, substituted imidazoles and more, these are however expensive and corrosive compounds.

P450 genes involved in insecticide resistance in agriculturally-economic crop pests or disease vectors, that have been identified include: CYP6CM1, conferring resistance to imidacloprid in tobacco whitefly, *Bemisia tabaci*; CYP6CY3 conferring resistance to neonicotinoid insecticides in peach-potato aphid, *Myzus persicae*; CYP6BQ23 confers resistance to pyrethroids in pollen beetle (*M. aeneus*); CYP9A12, CYP9A14, CYP6B7 confer resistance to pyrethroids in *H. armigera*; CYP6Z1, CYP6Z2, CYP6M2, CYP6P3 and CYP325A3 confer resistance to pyrethroids in mosquito species *An. Gambiae*.

Enhanced esterase production can result in insecticide resistance. A good example can be found in *M. persicae* where the esterase E4 or FE4 can hydrolyse or sequester a broad range of pesticides. Amplified esterases conferring resistance have also been identified in *B. tabaci, H. armigera*, mosquito species, *P. xylostella* etc.

We have now found that certain unsaturated organic acids and their derivatives are particular effective as inhibitors for the P450 enzymes. We have also found that they enhance insect mortality when used with insecticides based on pyrethroids and neonicotinoids and in particular synthetic pyrethroids.

We have also found that these unsaturated organic acids and their derivatives are particular effective as inhibitors for the esterase enzymes. We have also found that they enhance insect mortality when with insecticides based on pyrethroids and neonicotinoids and in particular with synthetic pyrethroids.

The unsaturated organic acids and their derivatives may also be used as synergists which inhibit enzymes to enhance the performance of herbicides and fungicides.

Although any unsaturated acid and its derivatives may be used we prefer that the unsaturated organic acids and their derivatives are naturally occurring materials or are derived from naturally occurring materials.

We have also found that in order to be an effective inhibitor typically the unsaturated organic acid or its derivative are preferably used in an amount of from 5 to 1000 g per hectare more preferably from 5 to 500 g per hectare. We have found that the use can also reduce the requirement of the amount of pesticide active ingredient required for a particular performance by at least 50% as compared to when the synergist is not used.

The unsaturated acids and their derivatives which are used in this invention are C6 to C24 mono- and polyunsaturated acids, their anhydrides, esters or their alkali or alkaline earth metal salts. In particular we prefer to use C8 to C18 mono- or polyunsaturated acids or their alkali metal salts. We further prefer that the C6 to C24 acids are derived from naturally occurring products such as from natural oil products such as sunflower oil, palm oil, olive oil, and other vegetable oils, soya chestnuts and horse chestnuts, which are usually obtained by extraction as mixtures of mono- or poly-unsaturated acids and where mixtures are used the average number of carbon atoms in the acid mixture should be in the C6 to C24 range. The free acids and the alkali metal salts of these acids are particularly preferred materials.

The C6 to C24 mono- and polyunsaturated acid used in the invention is typically a linear C6 to C24 mono- and polyunsaturated acid and thus has the formula RCOOH wherein R is a linear mono- or polyunsaturated hydrocarbon radical having from 6 to 24 carbons. Thus, the C6 to C24 mono- and polyunsaturated acid may be selected from myristoleic acid (C14:1), palmitoleic acid (C16:1) sapienic acid (C16:1), α-linolenic acid (C18:3), stearidonic acid (C18:4), eicosapentaenoic acid (C20:5), docosahexaenoic acid (C22:6), linoleic acid (C18:2), γ-linolenic acid (C18:3), dihomo-γ-linolenic acid (C20:3), arachidonic acid (C20:4), adrenic acid (C22:4), palmitoleic acid (C16:1), vaccenic acid (C18:1), paullinic acid (C20:1), oleic acid (C18:1), elaidic acid (Ctrans-18:1), gondoic acid (C20:1), erucic acid (C22:1), nervonic acid (C24:1), mead acid (C20:3) and derivatives thereof.

The notation CM:N fatty (where M and N are integers), as used herein, means that the fatty acid comprises M carbon atoms and N double bonds. The N double bonds may be at any position (cis or trans configuration), although two double bonds are not usually adjacent (i.e. bonded to the same carbon atom). Thus, C18:0 (or simply C18) covers only octadecanoic acid (stearic acid) and C18:1 includes all fatty acids having 18 carbons and one double bond, such as oleic acid ((Z)-octadec-9-enoic acid) and vaccenic acid ((E)-octadec-11-enoic acid).

The C6 to C24 mono- and polyunsaturated acid may for instance be selected from C12:1 fatty acids, C12:2 fatty acids, C14:1 fatty acid, C14:2 fatty acids, C16:1 fatty acids, C16:2 fatty acids, C18:1 fatty acids, C18:2 fatty acids, C18:3 fatty acids, and C20:1 fatty acids, and derivates thereof.

An anhydride of a C6 to C24 mono- and polyunsaturated acid is typically a compound of formula RC(O)OC(O)R' wherein R is a linear mono- or polyunsaturated hydrocarbon radical having from 6 to 24 carbons and R' is a hydrocarbon radical having from 1 to 30 carbons, for instance a linear mono- or polyunsaturated hydrocarbon radical having from 6 to 24 carbons.

An ester of a C6 to C24 mono- and polyunsaturated acid is typically a compound of formula RC(O)OR' wherein R is a linear mono- or polyunsaturated hydrocarbon radical having from 6 to 24 carbons and R' is a hydrocarbon radical having from 1 to 30 carbons, for instance an alkyl group having from 1 to 4 carbons.

An alkali or alkaline earth metal salt of an acid is typically a lithium, sodium, potassium or rubidium salt (alkali metal salt) or a magnesium, calcium or strontium salt (alkaline earth metal salt).

The C6 to C24 mono- and polyunsaturated acid may be oleic acid, linoleic acid or a derivative thereof.

Many nuts and fruits contain a mixture of unsaturated fatty acids and our preferred source of materials is *Aesculus hippocastanum* which is known to contain typically 350 g/Kg oleic and linoleic acids. (Zalatonov et al). Other preferred sources are the nut (acorn) of the oak tree (Genus *Quercus*) and ground coffee beans (the seed of the coffee plant). Biproducts of olive oil production are another preferred source.

Although not essential we prefer that the unsaturated acid or its derivative be used in a manner that allows it to interact with the insect, fungus or weed prior to subjecting the insect, fungus or weed to the insecticide, fungicide or herbicide. This may be accomplished by supplying the unsaturated acid and the pesticide, in a single formation in which the pesticide is provided in a slow release form. Alternatively and as is preferred the C6 to C24 mono- or polyunsaturated acid or its derivative is first applied to the crop followed by application of the pesticide. The pesticide is preferably applied within one to five hours of the application of the C6 to C24 mono-polyunsaturated acid or its derivative.

The invention is applicable to pesticides, particularly insecticides and more particularly to both synthetic and naturally occurring pyrethroids but is particularly useful with synthetic pyrethroids where it has been found to have an improved effect compared with PBO. Typical synthetic pyrethroids include permethrin, deltamethrin, fenvalerate, esfenvalerate, cyhalothrin, lambda-cyhalothrin, bifenthrin, cyfluthrin, tefluthrin, ethofenprox, tetramethrin, cypermethrins, fluvalinate, allethrin, tetramethrin, bioallethrin and zeta cypermethrin. However, the invention is also useful with natural pyrethrum insecticides.

Examples of neonicotinoids to which this invention is applicable include, but is not limited to include: imidacloprid, acetamiprid, nitenpyram, thiacloprid, thiamethoxam, clothianidin, dinotefuran.

The invention may also be applied to spinosin and chlorantraniliprol insecticides.

The pesticide formulation may comprise α-cypermethrin and potassium salts of one or more C14-C18 mono- or polyunsaturated fatty acids. The pesticide formulation may comprise α-cypermethrin and oleic acid. The pesticide formulation may comprise α-cypermethrin and linoleic acid.

The preferred pesticide formulations of this invention are adapted for spraying onto crops and are typically aqueous emulsions or solutions of the C6 to C24 mono- or polyunsaturated acid or its derivative and the pesticide and which may be separate solutions for sequential application or as a single formulation. We prefer that the C6 to C24 mono- or polyunsaturated acid or its derivative is water soluble. Preferred aqueous formulations for agricultural spraying contain from 5 to 500 g per hectare of the C6 to C24 mono- or poly unsaturated acid or its derivatives with the balance being water. Other additives such as antioxidants and viscosity modifiers may be included as may emulsifiers if the aqueous formulation is an emulsion. The amount of formulation that should be employed depends upon the target but typically we have found that formulations that provide from 50 to 250 grams of the C6 to C24 carboxylic acid or its derivative per hectare, preferably 75 to 150 grams per hectare are effective.

Where the invention is used in its preferred form as a synergist for pyrethroids or neonicotinoids insecticides the pyrethroid or the neonicotinoid employed will depend upon the insect that is to be targeted which may in turn depend upon the crop in question. Equally the effective treat rate will depend upon the insect that is to be targeted which may also depend upon the crop to be treated. Generally we found that the registered field rate is effective, but the invention may allow a reduction of this rate in some situations.

The invention is most preferably used in the control of pests selected from insects, arachnids, Helminths and in the control of grasses and weeds and fungi particularly in crops.

The invention can be used against a variety of pests including, but not limited to, the following families of mites:

Tetranychidae: Examples: *Tetranychus urticae* (two-spotted mite), *T. pacificus* (Pacific mite), *T. mcdanieli* (McDaniel mite), *T. turkestani* (strawberry mite), *Panonychus ulni* (European red mite), *P. citri* (citrus red mite), *Oligonychus pratensis* (Banks grass mite), *O. punicae* (avocado brown mite), *Eutetranychus hicoriae* (pecan leaf scorch mite), *Byrobia praetiosa* (clover mite). Eriophyidae (rust and blister mites): Examples: *Phyllocoptruta oleivora* (citrus rust mite), *Eriophyes sheldoni* (citrus bud mite), *E. erinea* (walnut blister mite), *Epitrimerus pyri* (pear rust mite), *Aculops lycopersici* (tomato russet mite).

Tenuipalpidae: Examples: *Brevipalpus lewisi* (citrus flat mite), *B. phoenicis* (red and black flat mite), *Dolichotetranychus floridanus* (pineapple false spider mite).

Tarsenomidae: Examples: *Steneotarsonemus bancrofti* (sugarcane stalk mite), *S. ananas* (pineapple tarsenomid), *S. pallidus* (cyclamen *Acarapis woodi* (honeybee mite).

The invention can be used against the following families of sucking insects:

Aleyrodidae (whiteflies): Examples: *Bemisia tabaci* (sweetpotato whitefly), *Trialeurodes vaporariorum* (greenhouse whitefly), *Siphoninus phillyreae* (ash whitefly), *Dialeurodes citrifolii* (cloudywinged whitefly), *Aleurocanthus woglumi* (citrus blackfly). Aphids, including peach-potato aphid (*Myzus persicae*), cotton aphid (*Aphis gossypii*).

Nitidulidae: examples *Meligethes aeneus* (pollen beetle).

Psyllidae (psyllids): Examples: *Psylla pyricol* (pear psylla), *Paratrioza cockerelli* (potato/tomato psyllid).

In a further embodiment the invention can be used against leaf mining flies of the order Diptera and family Agromyzidae. Examples of these flies are Liriomyza complex (serpentine leafminers), *Phytomyza syngenesiae* (chrysanthemum leafminer), *Agromyza frontella* (alfalfa blotch leafminer), *Ophiomyia phaseoli* (bean fly). Diptera: mosquitoes, subfamily Anophelinae and subfamily Culicinae.

Other target pests include, but are not limited to, Thysanoptera (thrips), Hymenoptera (wasps), Hemiptera (bugs), Cicadellidae (leafhoppers), Membracidae (treehoppers), Coccidae (scales), Pseudococcidae (mealybugs), Diaspididae (scales), and Solenopsis (fire ants). The invention is also useful against mosquitos particularly in tropical and sub tropical climates.

The present invention is illustrated but in no way limited by reference to the following Examples.

Example 1

Houseflies (*Musca domestica*) were treated with 1 µL of a diagnostic concentration (0.0025 g $L^{-1}$) of α-cypermethrin, such that about 20% of the flies had died after 24 hrs.

With the addition of 1% 'Syn A', (i.e. 10 µg/fly) the potassium salts of fatty acids (C14-C18) obtained as a by-product of olive oil production, the mortality increased to about 70% after 24 hours. The potassium salt synergist was applied first, and the insecticide was applied within 1 hr of the application of the synergist.

The mortality rate when Syn A was used on its own was about 10%.

The results are shown in FIG. 1.

Example 2

The house fly (*Musca domestica*) when exposed to a low mortality (0.0025 $g^{-1}$) dose of the synthetic pyrethroid in the presence of the synergists AHI-1 (24 ug/fly) and AHI-2 (40 ug/fly) where AH-1 is the ethanol extract of the seed of *Aesculus hippocastanum* which produced a mixture containing about 50% oleic acid and 30% linoleic acid and AH-2 is the ethanol extract of the fruit of *Aesculus hippocastanum* which produced a mixture containing about 40% oleic acid and 30% linoleic acid An approximate doubling of the insecticide's activity was achieved and the synergists were essentially non-toxic to the flies. Insects were treated by topical application of the synergists followed by the insecticide 3 hours later.

Figure 2:
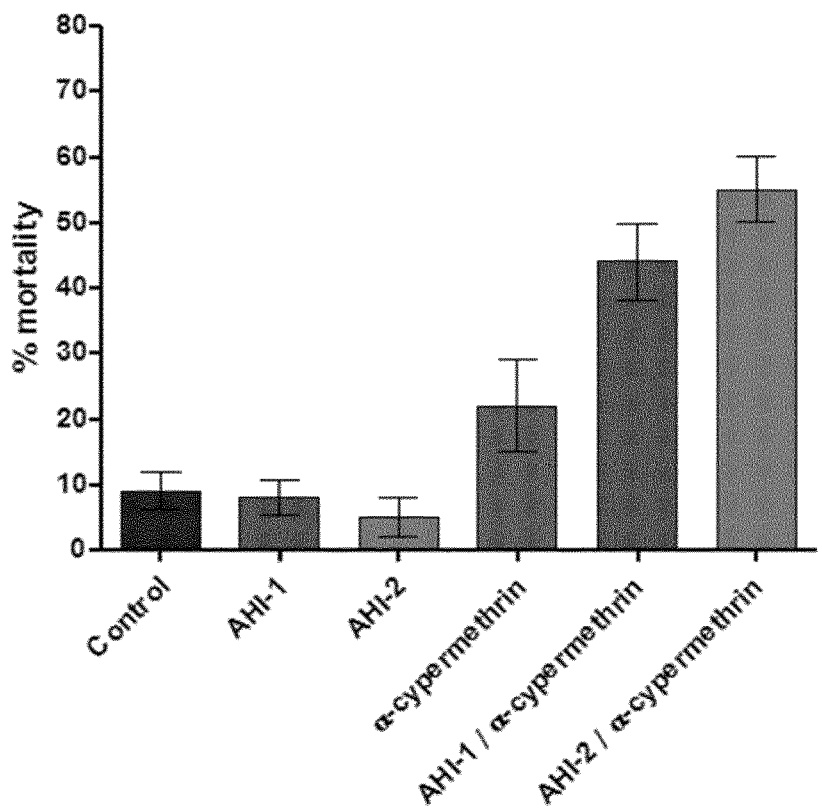
FIG. 2 is a graph illustrating the mortality rates of Example 2.

The results are shown in FIG. 2. Comparative data for the synthetic synergist piperonyl butoxide (PBO) is included in FIG. 2.

Example 3

Example 3 shows the inhibition of purified resistance-associated esterase, E4, by AH-1 and AH-2 as used in Example 2. The assay used 1 mM para-nitrophenyl acetate as a substrate. 10 µL dilute E4 in 40 µL phosphate buffer (pH 7.0) was incubated with 3 µL 1% synergist for 10 minutes. 200 µL of 1 mM para-nitrophenyl acetate was added and the remaining activity was measured at 405 nm in a microplate spectrophotometer (Molecular Devices). Inhibition by the same concentration of PBO is shown for comparison.

Figure 3:
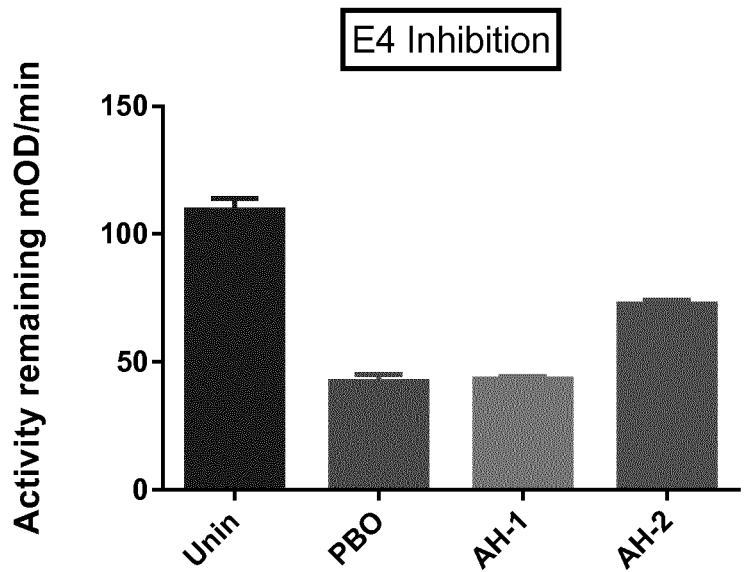
FIG. 3 is a graph illustrating the results of Example 3.

The results are shown in FIG. 3.

Example 4

Example 4 shows the increased mortality when 500 uL of a diagnostic concentration of alpha-cypermethrin (0.0001%) is mixed with AH-1 (1 mg) or AH-2 (2 mg) as used in Example 2 before exposing to pollen beetle, *Meligethes aeneus*. Mortality was determined after 24 hrs. The bioassay were conducted in glass vials.

Figure 4:
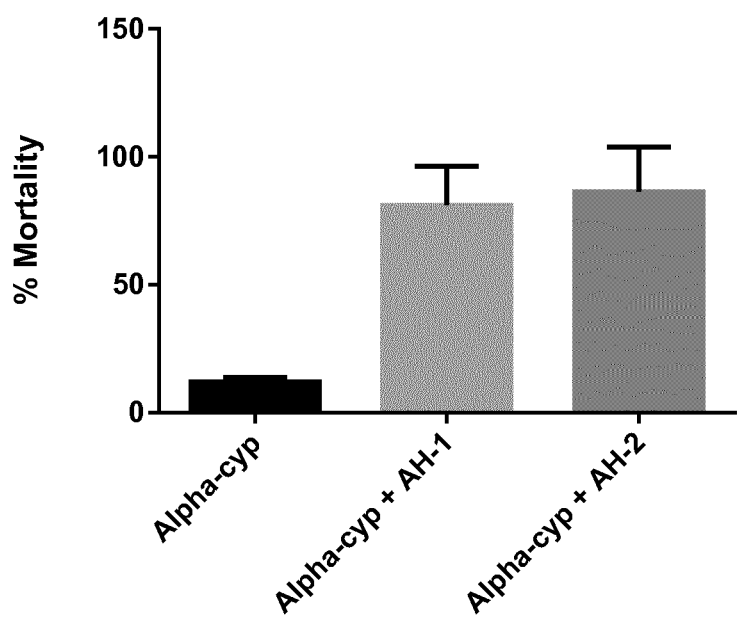
FIG. 4 is a graph illustrating the mortality rates of Example 4.

The results are shown in FIG. 4.

Example 5

Example 5 shows the inhibition of P450 activity derived from insecticide-resistant B-type *B. tabaci*, when incubated with 1% oleic and 1% linoleic acid (30 ug/incubation). P450 activity was measured by the demethylation of ethoxycoumarin. 50 µL of the enzyme in the presence/absence of synergists was incubated for 10 minutes after which 80 ml of 0.5 mm 7-ethoxycoumarin in a phosphate buffer (pH 7.8) was added/incubated for a further 5 minutes at 30° C. after which 10 µL of 9.6 mm NaDPH was added. Fluorometric units (Fu) were measured with excitation wavelengths of 370 nm and 460 nm.

Figure 5:
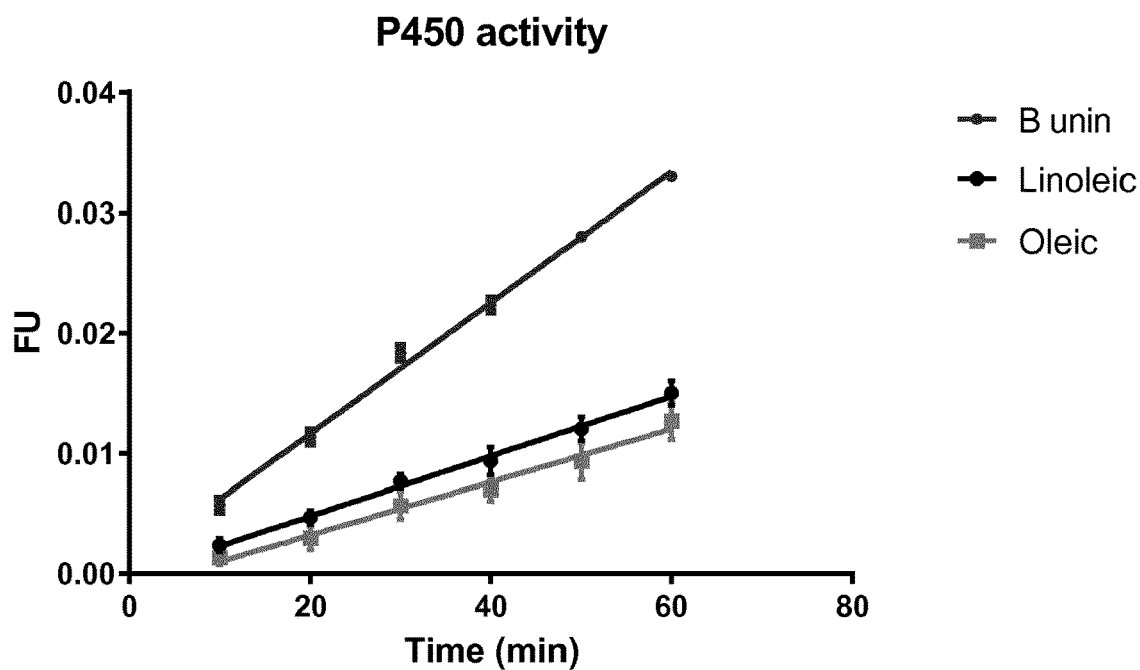
FIG. 5 is a graph illustrating the results of Example 5.

The results are shown in FIG. 5.

Example 6

Example 6 shows the inhibition of resistance-associated esterase, E4, after treatment with oleic and linoleic acids in the same way as in Example 3.

Figure 6:
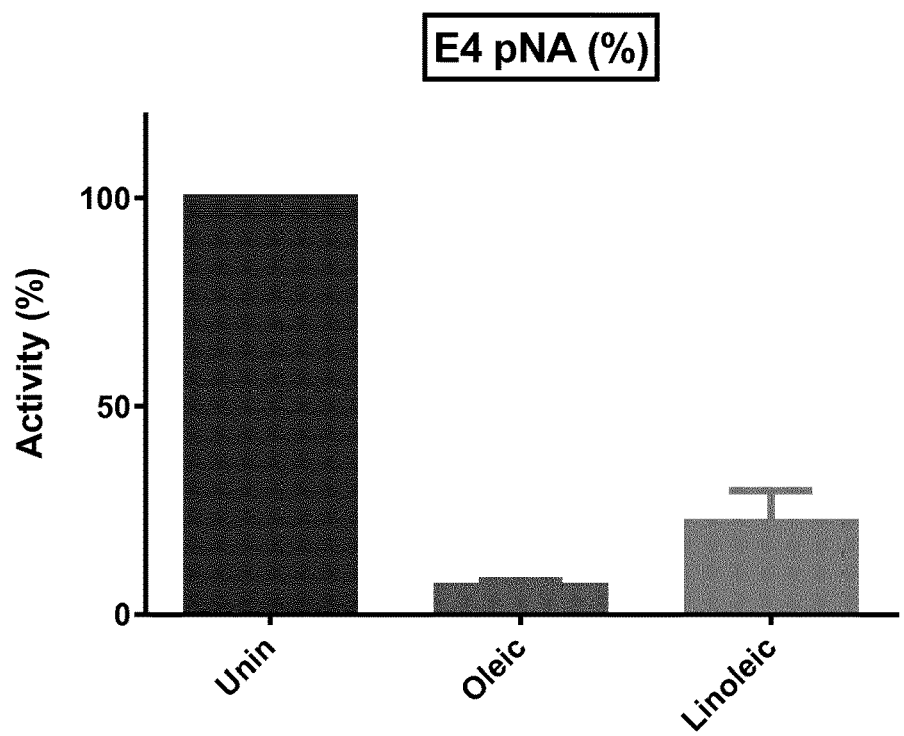
FIG. 6 is a graph illustrating the activity rates of Example 6.

The results are shown in FIG. 6.

Example 7

Example 7 shows inhibition of P450 activity derived from *Meligethes aeneus* following treatment with equal concentrations of PBO, Syn A, AH-1 and AH-2. (30 ug/incubation) as used in Example 5.

Figure 7:
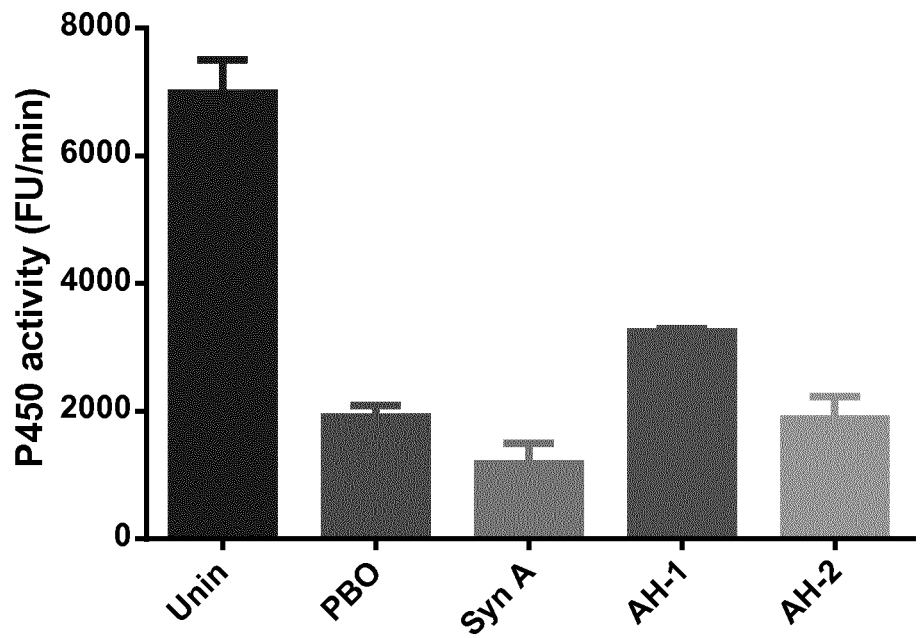
FIG. 7 is a graph illustrating the results of Example 7.

The results are shown in FIG. 7.

Example 8

Inhibition of P450 activity from *Meligethes aeneus* (pollen beetle) following incubation with equal concentrations of Syn-A as used in Example 1, Syn-B, Syn-C and PBO was assessed.

Syn-B is an ethanolic extraction of acorns; Syn-C is an ethanolic extraction of (used) coffee beans.

P450 activity was measured fluorometrically by the demethylation of ethoxycoumarin (ECOD) method used in Example 5, with 0.1% synergist extracts used.

Both acorn and coffee contain high percentage of unsaturated fatty acids as described in Charef et al. (2008) and Martin et al. (2001) respectively.

Figure 8:
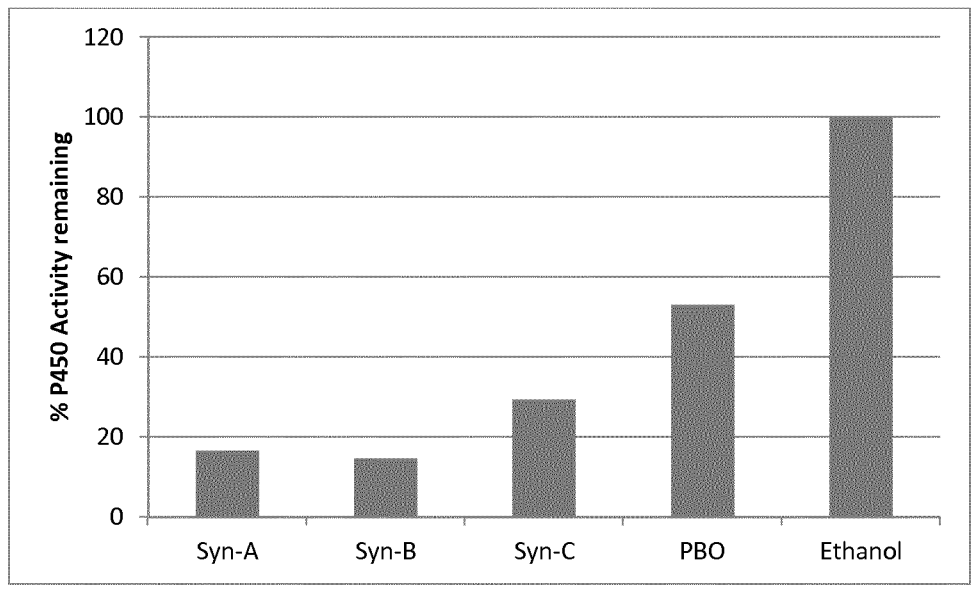
FIG. 8 is a graph illustrating the results of Example 8.

The results are shown in FIG. 8.

Example 9

Insecticide-resistant *Musca domestica*, dosed with 1 µL of acetone (control), 10 g/L Syn-A, 5 g/L imidacloprid, or a mix of the two (at twice concentration). Mortality was measured after 24 hrs.

Figure 9:
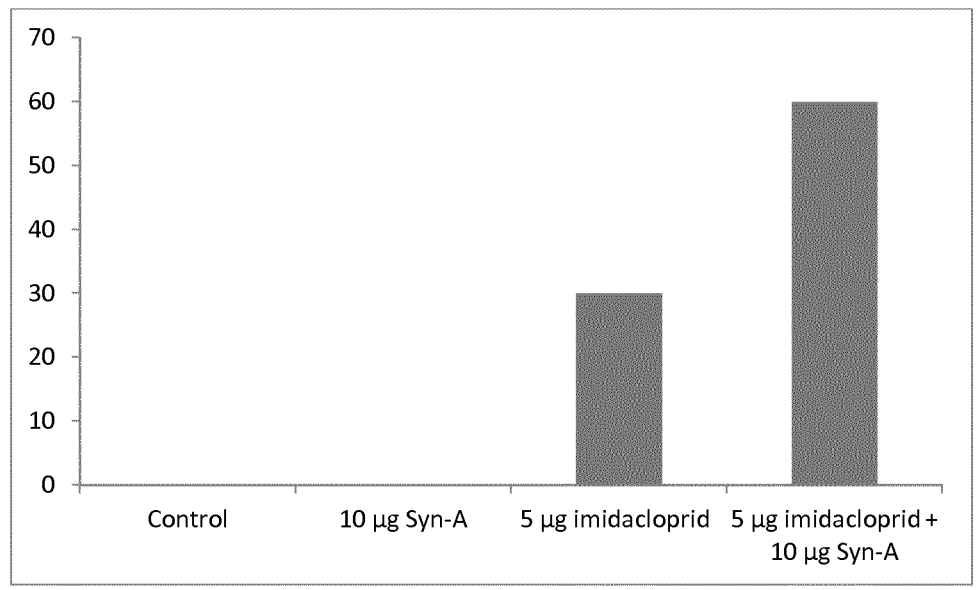
FIG. 9 is a graph illustrating the results of Example 9.

The results are shown in FIG. 9.

Example 10

Example 10 shows the inhibition of resistance-associated esterase, E4, after treatment with Syn-B and Syn-C (as used in Example 8) using the method of Example 3, with the exception that 0.1% extracts of synergists were used.

Figure 10:
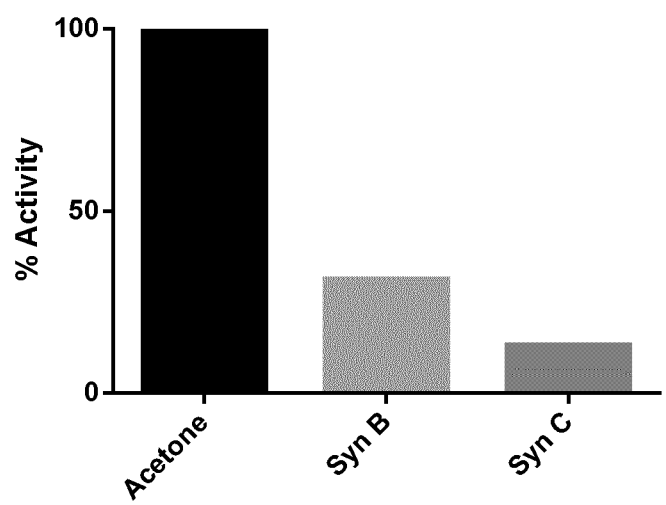
FIG. 10 is a graph illustrating the activity rates of Example 10.

The results are shown in FIG. 10.

The invention claimed is:

1. A pesticide formulation comprising: (i) an aqueous emulsion or solution of a C6 to C24 mono- or polyunsaturated acid or its derivatives; and (ii) a pesticide;
    wherein the C6 to C24 mono- or polyunsaturated acid or its derivatives are naturally occurring products selected from vegetable oils, soya, acorns, chestnuts, horse chestnuts, and coffee, or are derived therefrom and the C6 to C24 mono- or polyunsaturated acid or its derivatives are an extraction of mono- or polyunsaturated acids from the naturally occurring products;
    wherein the derivatives are selected from anhydrides, or alkali or alkaline earth metal salts;
    wherein the C6 to C24 mono- or polyunsaturated acid or its derivatives comprise a mixture of acids, and an average number of carbon atoms in the acids in the mixture of acids is in the C6 to C24 range; and
    wherein the pesticide is an insecticide.

2. The pesticide formulation according to any of claim 1, comprising separate solutions or emulsions of the C6 to C24 mono- or polyunsaturated acid or its derivatives and the pesticide, the separate solutions or emulsions being applied sequentially onto one or more crops.

3. The pesticide formulation according to claim 1, wherein the pesticide is in slow-release form.

4. A process for protection of crops; comprising: applying the pesticide formulation of claim 1 to the crops,
    wherein the C6 to C24 mono- or polyunsaturated acid or its derivatives is applied in an amount of from 5 to 1000 grams per hectare.

5. The process according to claim 4, wherein the C6 to C24 mono- or polyunsaturated acid or its derivatives is applied before application of the pesticide.

6. The process according to claim 4, wherein the C6 to C24 mono- or polyunsaturated acid or its derivatives and the pesticide are applied as a single formulation wherein the pesticide is in a slow-release form.

7. The pesticide formulation according to claim 1, wherein the C6 to C24 mono- or polyunsaturated acid or its derivatives are free of esterification.

8. The process according to claim 4, wherein the C6 to C24 mono- or polyunsaturated acid or its derivatives are present in a range of 5 to 500 grams per hectare being treated.

* * * * *